United States Patent
Geroni et al.

(10) Patent No.: US 6,586,428 B2
(45) Date of Patent: Jul. 1, 2003

(54) COMBINED PREPARATIONS COMPRISING MORPHOLINE ANTHRACYCLINES AND ANTICANCER AGENT

(75) Inventors: Maria Cristina Geroni, Milan (IT); Marina Ripamonti, Milan (IT); Michele Caruso, Milan (IT); Antonino Suarato, Milan (IT)

(73) Assignee: Pharmacia Italia, S.p.A., Milan (IT)

( * ) Notice: Subject to any disclaimer, the term of this patent is extended or adjusted under 35 U.S.C. 154(b) by 0 days.

(21) Appl. No.: 10/284,144

(22) Filed: Oct. 31, 2002

(65) Prior Publication Data

US 2003/0087839 A1 May 8, 2003

Related U.S. Application Data

(63) Continuation of application No. 09/926,392, filed as application No. PCT/EP00/02923 on Apr. 4, 2000.

(30) Foreign Application Priority Data

Apr. 26, 1999 (GB) .............................................. 9909925

(51) Int. Cl.[7] .................. A61K 31/5377; C07D 413/04
(52) U.S. Cl. ..................................... 514/231.5; 544/149
(58) Field of Search ........................ 544/149; 514/231.5

(56) References Cited

U.S. PATENT DOCUMENTS

| | | | |
|---|---|---|---|
| 4,710,564 A | 12/1987 | Otake et al. ................. | 544/149 |
| 5,902,809 A | 5/1999 | Adekenov ................ | 514/231.5 |

FOREIGN PATENT DOCUMENTS

| WO | WO 99/48503 | 9/1999 |
|---|---|---|
| WO | WO 00/15203 | 3/2000 |

OTHER PUBLICATIONS

Kishimoto et al, Anti–Cancer Drugs, vol. 10, No. 3, pp. 267–273, Mar. 1999.
Hiraoka et al, Japanese Journal of Cancer and Chemotherapy, vol. 26, No. 1, pp. 93–99, Jan. 1999.
Ohe et al, Cancer Research, vol. 49, No. 15, pp. 4098–4102, Aug. 1989.
Van Der Graaf et al, Cancer Chemotherapy and Pharmacology, vol. 35, No. 4, pp. 345–348, 1995.
Alvino et al, Cancer Chemotherapy and Pharmacology, vol. 40, No. 2, pp. 180–184, 1997.
Taub et al, Proceedings of the Annual Meeting of the American Society of Clinical Oncology, vol. 16, p. A1831, 1997.
Vasey et al, Cancer Research, vol. 55, No. 10, pp. 2090–2096, 1995.
Watanabe et al, Cancer Research, vol. 48, No. 23, pp. 6653–6657, 1988.
Watanabe et al, Cancer Research, vol. 51, No. 1, pp. 157–161, 1991.
Sola et al, Cancer Chemotherapy and Pharmacology, vol. 43, No. 3, pp. 241–246, 1999.

*Primary Examiner*—Joseph K. McKane
*Assistant Examiner*—Rebecca Anderson
(74) *Attorney, Agent, or Firm*—McDonnell Boehnen Hulbert & Berghoff

(57) ABSTRACT

The present invention relates to combined preparations comprising a morpholinyl anthracycline administered in combination anticancer agents chosen from an alkylating agent, an antimetabolite, a topoisomerase II inihbitor, a topoisomerase I inhibitor, an antimitotic drug and a platinum derivative, which are useful anticancer therapy, particularly in the treatment of a primary or metastatic liver cancer.

22 Claims, No Drawings

COMBINED PREPARATIONS COMPRISING MORPHOLINE ANTHRACYCLINES AND ANTICANCER AGENT

The present invention pertains to the field of neoplastic diseases theraphy. In particular, the present invention refers to the synergic anticancer effect displayed by an anthracycline derivative administered in combination with at least another pharmaceutical substance effective in anticancer theraphy.

Cancers are a leading cause of death in animals and humans; surgery, radiation and chemotherapy are the useful means to fight cancers.

In particular, combined chemotherapy, designed to treat cancer by using more than one drug in combination or association, is a well accepted modality of treatment of neoplastic diseases.

Several efforts have been and are still being undertaken in order to select antitumor combinations more and more active and safe to be administered to a patient suffering from a cancer.

The increase of the antitumor efficacy of a known antitumor compound by administering the same in combination with one or more different antitumor compounds in order to obtain a therapeutic synergy, is a strongly felt need in the field of anticancer theraphy.

The present invention fulfill such a need by providing an anthracycline derivative which a is morpholinyl anthracycline, administered in combination with at least another pharmaceutical substance effective in anticancer theraphy, so that a synergistic effect can be revealed.

It is therefore a first object of the present invention combined preparations comprising a morpholinyl anthracycline administered in combination with at least another pharmaceutical substance effective in anticancer theraphy chosen from an alkylating agent, an antimetabolite, a topoisomerase II inhibitor, a topoisomerase I inhibitor, an antimitotic drug and a platinum derivative.

Anthracycline derivatives according to this invention are morpholinyl anthracyclines having formula (I) and (II)

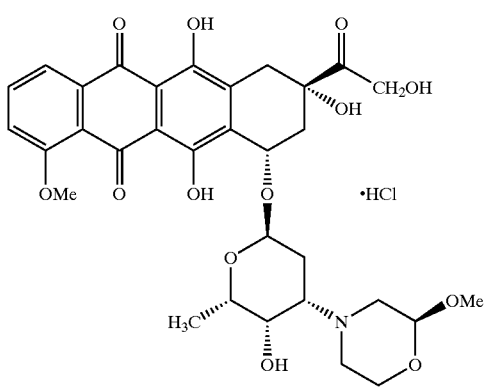

(I)

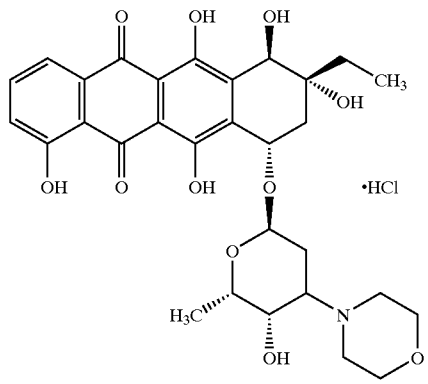

(II)

The chemical names of the morpholinyl anthracyclines of formula (I) and (II) are 3'-deamino-3'-(2-methoxy-4-morpholinyl)doxorubicin. HCl (I), also known as methoxy-morpholino doxorubicin (MMDX, internal code PNU 152243), and 3'-deamino-3'(4-morpholinyl)-13-deoxo-10-hydroxy-carminomycin (II), also known as MX2.

MMDX is a doxorubicin derivative obtained with the substitution of the $-NH_2$ at position 3' in the sugar moiety with a methoxymorpholino group. This compound, synthesised in the course of a research program aimed at identifying new anthracyclines with at least partially novel modes of action and possessing broad spectrum of activity, was disclosed and claimed in Bargiotti et al., U.S. Pat. No. 4,672,057.

MMDX is active in vitro and in vivo on tumor cells resistant to anthracyclines and presenting the mdr phenotype, this last mechanism being recognised to occur also in man.

No cross-resistance was observed on tumor cells resistant to L-PAM or cisplatin (cDDP), or on cells resistant to Topoisomerase II inhibitors (at-multidrug resistant).

MMDX is active after i.p., i.v. or oral administration, with good antitumor activity on murine leukemias, and on solid murine and human tumor models.

The compound differs from most anthracyclines in being highly potent when administered in vivo, the optimal i.v. dose being at least 80 fold less than that of doxorubicin.

The high lipophilicity of the molecule, which confers to the compound the ability to reach high intracellular concentrations and is most likely one of the reasons of its efficacy on resistant models, makes it effective also after oral administration.

MX2, a morpholinyl anthracycline belonging to the family of 3'-deamine-3'(4-morpholinyl) derivatives of 10-hydroxy-13-deoxocarminomycin, was described and claimed in Otake et al., U.S. Pat. No. 4,710,564.

MX2 is active in vitro and in vivo on tumor cells resistant to anthracyclines and presenting mdr phenotype.

No cross-resistance was observed on tumor cells resistant to CTX, L-Pam and cDDP.

MX2 is active in vivo after i.p., i.v. and oral administration, with good antileukemic and antitumor activity on murine and human tumor models. MX2 is highly lipophilic and less cardiotoxic than Doxorubicin. The major dose limiting factor of MX2 is myelosuppression.

Among pharmaceutical substances effective in anticancer theraphy which may be used in association or in combination with a morpholinyl anthracycline of formula (I) or (II) as defined above, there may be mentioned alkylating agents such as, e.g., mitomycin C, cyclophosphamide, busulfan, ifosfamide, isosfamide, melphalan, hexamethylmelamine, thiotepa, chlorambucil, or dacarbazine; antimetabolites such as, e.g., gemcitabine, capecitabine, 5-fluorouracil, cytarabine, 2-fluorodeoxy cytidine, methotrexate, idatrexate, tomudex or trimetrexate; topoisomerase II inhibitors such as, e.g., doxorubicin, epirubicin, etoposide, teniposide or mitoxantrone; topoisomerase I inhibitors such as, e.g., irinotecan (CPT-11), 7-ethyl-10-hydroxy-camptothecin (SN-38) or topotecan; antimitotic drugs such as, e.g., paclitaxel, docetaxel, vinblastine, vincristine or vinorelbine; and platinum derivatives such as, e.g., cisplatin, oxaliplatin, spiroplatinum or carboplatinum.

As used herein, "anticancer therapy" refers to all types of therapies for treating cancers or neoplasms or malignant tumors found in mmls comprising humans, including leukemiae, melanoma, liver, breast, ovary, prostate, stomach, pancreas, lung, kidney, colon and central nervous system tumors.

The administration of the costituents of the combined preparations of the present invention can be made simultaneously, separately or sequentially.

It is therefore another object of the present invention the simultaneous, separate or sequential use of the combined preparations of the invention in anticancer theraphy.

As an example, a morpholinyl anthracycline of formula (I) or (II) as defined above can be administered before the other anticancer drug; a particular example refers to the morpholinyl anthracycline of formula (I) administered on day 1 and 2 followed by cisplatin on day 3.

A preferred combined preparation according to the invention comprises a morpholinyl anthracycline of formula (I) or (II) as defined above and a platinum derivative, in particular cisplatin. A more preferred combined preparation according to the invention comprises a morpholinyl anthracycline of formula (I) and cisplatin.

As already said, combined preparations according to the invention may be used in anticancer therapy. In a preferred embodiment, combined preparations of the invention may be useful for treating a liver cancer, for example a liver cancer primarily confined to the liver such as, e.g. an hepatocellular carcinoma or a cholangiocarcinoma, or liver metastases.

The costituents of the combined preparations according to the invention can be administered to a patient in any acceptable manner that is medically acceptable including orally, parenterally, or with locoregional therapeutic approaches such as, e.g., implants. Oral administration includes administering the costituents of the combined preparation in a suitable oral form such as, e.g., tablets, capsules, lozenges, suspensions, solutions, emulsions, powders, syrups and the like. Parenteral administration includes administering the costituents of the combined preparation by subcutaneous, intravenous or intramuscular injections. Implants include intra artherial implants, for example an intrahepatic artheryy implant.

Injections and implants are preferred administration routes because they permit precise control of the timing and dosage levels used for administration.

For example, for treating a patient suffering from a liver cancer as defined above, simultaneous, separate or sequential intrahepatic administration of the costituents of the combined preparation may be performed via the hepatic artheryy. More precisely, the costituents of the combined preparation may be administered to a patient with either a hepatic metastatic cancer, or with previously untreated primary liver carcinoma, via the hepatic artheryy directly into the lateral entry of an i.v. line inserted into the bung of an intrahepatic potacath or via a catheter inserted into the hepatic artery.

In a particular embodiment of the present invention, MMDX may be administered via the hepatic artheryy as an infusion; the appropriate dose of MMDX, preferably previously dissolved in saline solution, may be mixed with a suitable amount, for example an amount ranging from 1 ml to 100 ml of an agent, for example iodized oil (LIPIODOL™), which remains selectively in a liver tumor after its injection through the hepatic artheryy. The actual preferred method and order of administration of the constituents of the combined preparation of the invention may vary according to, inter alia, the particular pharmaceutical formulation of the morpholinyl anthracycline (I) or (II) as defined above being utilized, the particular pharmaceutical formulation of the other anticancer agent being utilized, the particular cancer being treated, the severity of the disease state being treated, and the particular patient being treated. The dosage ranges for the administration of the combined preparations according to the invention may vary with the age, condition, sex and extent of the disease in the patient and can be determined by one of skill in the art.

The dosage regimen must therefore be tailored to the particular of the patient's conditions, response and associate treatments, in a manner which is conventional for any therapy, and may need to be adjusted in response to changes in conditions and/or in light of other clinical conditions.

The present invention also provides, in another aspect, products containing a morpholinyl anthracycline of formula (I) or (II) as defined above and at least another anticancer agent chosen from an alkylating agent, an antimetabolite, a topoisomerase II inhibitor, a topoisomerase I inhibitor, an antimitotic drug and a platinum derivative, as a combined preparation for simultaneous, separate or sequential use in anticancer theraphy.

The present invention also relates to pharmaceutical compositions comprising, mixed together, two or more active constituents of the combined preparations according to the invention and a pharmaceutically acceptable carrier or excipient.

It is therefore a further object of the present invention a pharmaceutical composition comprising a pharmaceutically acceptable carrier or excipient and, as an active ingredient, a morpholinyl anthacycline of formula (I) or (II) as defined above and at least another anticancer agent chosen from an alkylating agent, an antimetabolite, a topoisomerase II inhibitor, a topoisomerase I inhibitor, an antimitotic drug and a platinum derivative.

Pharmaceutical compositions according to the invention are useful in anticancer therapy. In particular, they may be useful for treating a liver cancer as defined above. Pharmaceutically acceptable carriers or excipients to be utilized in the preparation of a pharmaceutical composition according to the invention are well known to people skill in the art of formulating compounds in a form of pharmaceutical compositions.

For example, such pharmaceutical compositions may routinely contain, e.g., pharmaceutically acceptable salts, buffering agents, preservatives and/or compatible carriers. As used herein, "pharmaceutically acceptable carrier" refers to one or more compatible solid or liquid filler, diluent or encapsulating substances which are suitable for administration to mammals including humans.

Pharmaceutical compositions suitable for parenteral or intrahepatic administration are formulated in a sterile form. The sterile composition thus may be a sterile solution or suspension in a non-toxic parenterally acceptable diluent or solvent.

Pharmaceutical compositions for intrahepatic administration are formulated, for example, in a form which remains selectively in a liver tumor after their injection through the hepatic artery; LIPIODOL™ is a suitable carrier of anticancer agents which can be used for intrahepatic administration.

The amount of an active ingredient contained in the pharmaceutical composition according to the invention may vary quite videly depending upon many factors such as e.g. the administration route and the vehicle.

As an example, the pharmaceutical composition of the invention may contain from 0.1 mg to 100 mg of MMDX and from 1 mg to 1000 mg of a platinum derivative such as cisplatin.

A further aspect of the present invention is to provide a method of treating a mammal including a human, suffering from a cancer comprising administering to said mammal a morpholinyl anthracycline of formula (I) or (II) as defined above and at least another anticancer agent chosen from an alkylating agent, an antimetabolite, a topoisomerase II inhibitor, a topoisomerase I inhibitor, an antimitotic drug and a platinum derivative, in amounts effective to produce a synergistic anticancer effect.

A still further aspect of the present invention is to provide a method for lowering the side effects caused by anticancer theraphy with an anticancer agent in mammals, including humans, in need thereof, the method comprising administering to said mammal a combined preparation comprising a morpholinyl anthacycline of formula (I) or (II) as defined above and at least another anticancer agent chosen from an alkylating agent, an antimetabolite a topoisomerase II inhibitor, a topoisomerase I inhibitor, an antimitotic drug and a platinum derivative, in amounts effective to produce a synergistic anticancer effect.

In particular, the present invention provides a method of treating patients suffering from a primary or metastatic liver cancer.

By the term "a synergistic anticancer effect" as used herein is meant the inhibition of the growth tumor, preferably the complete regression of the tumor, administering an effective amount of the combination of a morpholinyl anthracycline of formula (I) or (II) as defined above and at least another anticancer agent chosen from an alkylating agent, an antimetabolite a topoisomerase II inhibitor, a topoisomerase I inhibitor, an antimitotic drug and a platinum derivative, in amounts effective to produce a synergistic anticancer effect to mammals, including humans.

By the term "administered" or "administering" as used herein is meant parenteral and/or oral and/or locoregional administration, as defined above. In the method of the subject invention, the morpholinyl anthracycline may be administered simultaneously with at least another anticancer agent chosen from an alkylating agent, an antimetabolite a topoisomerase II inhibitor, a topoisomerase I inhibitor, an antimitotic drug and a platinum derivative, or the compounds may be administered sequentially, in either order. It will be appreciated that the actual preferred method and order of administration will vary according to, inter alia, the particular formulation of the morpholinyl anthracycline of formula (I) or (II) being utilized, the particular formulation of the alkylating agent, of the antimetabolite, of the topoisomerase II inhibitor, of the topoisomerase I inhibitor, of the antimitotic drug or of the platinum derivative being utilized, the particular tumor model being treated, and the particular host being treated.

In the method of the subject invention, for the administration of the morpholinyl anthracycline of formula (I) or (II), the course of therapy generally employed is from about 0.1 mg/m$^2$ to about 100 mg/m$^2$ of body surface area. More preferably, the course of therapy employed is from about about 1 mg/m$^2$ to about 1000 mg/m$^2$ of body surface area.

In the method of the subject invention, for the administration of the alkylating agent the course of therapy generally employed is from about 10 mg/m$^2$ to about 100,000 mg/m$^2$ of body surface area. More preferably, the course therapy employed is from 180 mg/m$^2$ to about 16,000 mg/m$^2$ of body surface area.

In the method of the subject invention, for the administration of the antimetabolite the course of therapy generally employed is from about 0.1 mg/m$^2$ to about 1000 mg/m$^2$ of body surface area. More preferably, the course therapy employed is from 0.2 mg/m$^2$ to about 500 mg/m$^2$ of body surface area.

In the method of the subject invention, for the administration of the topoisomerase II inhibitor the course of therapy generally employed is from about 1 mg/m$^2$ to about 1000 mg/m$^2$ of body surface area. More preferably, the course therapy employed is from 10 mg/m$^2$ to about 500 mg/m$^2$ of body surface area.

In the method of the subject invention, for the administration of the topoisomerase I inhibitor the course of therapy generally employed is from about 1 mg/m$^2$ to about 1000 mg/m$^2$ of body surface area. More preferably, the course therapy employed is from 100 mg/m$^2$ to about 500 mg/m$^2$ of body surface area.

In the method of the subject invention, for the administration of the antimitotic drug the course of therapy generally employed is from about 1 mg/m$^2$ to about 1000 mg/m$^2$ of body surface area. More preferably, the course therapy employed is from 10 mg/m$^2$ to about 500 mg/m$^2$ of body surface area.

In the method of the subject invention, for the administration of the platinum derivative the course of therapy generally employed is from about 1 mg/m$^2$ to about 1000 mg/m$^2$ of body surface area. More preferably, the course therapy employed is from 10 mg/m2 to about 500 mg/m$^2$ of body surface area.

As already said, the anticancer therapy of the present invention is suitable for treating, e.g. breast, ovary, prostate, lung, colon, kidney, stomach, pancreas, liver, melanoma, leukemiae and central nervous system tumors in mammals, including humans; in particular it is suitable for treating a liver cancer.

The present invention also provides a therapeutic kit comprising, in suitable container means, a pharmaceutical formulation of a morpholinyl anthacycline of formula (I) or (II) as defined above and a pharmaceutical formulation of at least another anticancer agent chosen from an alkylating agent, an antimetabolite, a topoisomerase II inhibitor, a topoisomerase I inhibitor, an antimitotic drug and a platinum derivative. For example, in a kit according to the invention, the morpholinyl anthacycline and at least another anticancer agent chosen from an alkylating agent, an antimetabolite, a topoisomerase II inhibitor, a topoisomerase I inhibitor, an antimitotic drug and a platinum derivative are present within a single container means or within distinct container means. As a particular example, a kit comprises a pharmaceutical formulation of the morpholinyl anthracycline of formula (I)

as defined above and a pharmaceutical formulation of cisplatin, within distinct container means.

Kits according to the invention are intended for use in anticancer therapy as defined above, in particular for the treatment of a liver cancer.

As stated above, the effect of the combined administration of a morpholinyl anthracycline of formula (I) or (II) as defined above and of at least another pharmaceutical substance effective in anticancer theraphy such as an alkylating agent, an antimetabolite, a topoisomerase II inhibitor, a topoisomerase I inhibitor, an antimitotic drug or a platinum derivative, is significantly increased (synergic effect) without a parallel increased toxicity.

In other words, the combined theraphy of the present invention enhances the anticancer effects of the morpholinyl anthracycline (I) or (I) as defined above and of the other anticancer substance and thus yields the most effective and least toxic treatment for cancers.

The superadditive, actions of the combined preparations of the present invention are shown, for instance, by the following in vivo tests, which are illustrative, but not limiting of the combined preparations and methods of the present invention. Other suitable modifications and adaptations of a variety of conditions and paramenters normally encountered in clinical theraphy which are obvious to those skilled in the art are within the scope of this invention.

Table 1 shows the antileukemic activity on disseminated L1210 murine leukemia, (originally obtained from NCI) obtained combining the morpholinyl anthracycline of formula (I) (PNU-152243) with cisplatin (cDDP), a platinum derivative, which is a representative pharmaceutical substance effective in anticancer therapy.

TABLE 1

Antileukemic activity against disseminated L1210[1]
murine leukemia of PNU-152243 in combination with cDDP

| Compound | Treatment schedule | Dose[2] (mg/Kg/day) | ILS %[3] | Tox[4] | Statistical Analysis Two Ways ANOVA |
|---|---|---|---|---|---|
| PNU-152243 | iv + 1,2 | 0.05 | 50 | 0/10 | |
| cDDP | iv + 3 | 5.9 | 33 | 0/10 | |
| | | 7.7 | 33 | 0/10 | |
| PNU-152243 + cDDP | iv + 1,2 iv + 3 | 0.05 5.9 | 83 | 0/10 | P = 0.0034 Synergistic effect |
| PNU-152243 + CDDP | iv + 1,2 iv + 3 | 0.05 7.7 | 100 | 0/10 | P = 0.0036 Synergistic effect |

[1]L1210 murine leukemia was maintained in DBA/2 mice by weekly ip passages of $10^5$ cells/mouse-For experiments, $10^5$ cells/mouse were injected iv in CD2F1 mice on day 0.
[2]Treatment is given starting on day 1 after tumor transplantation (day 0)
[3]Increased in Life Span [(Median survival time of treated mice/median survival time of controls) × 100]-100
[4]Number of toxic deaths/number of mice The above reported data show that at doses of 5.9 and 7.7 mg/kg of cDDP administered alone on day 3, and at the dose of 0.05 mg/kg of PNU 152243 administered alone on day 1 and 2, were associated, without toxicity, ILS% values of 33, 33 and 50, respectively.

Data obtained combining administration of 0.05 mg/kg PNU 152243 on day 1 and 2 and 5.9 or 7.7 mg/kg of cddp on day 3, clearly indicates a significant increase (synergistic effect) in ILS% (83 and 100 respectively), demonstrating an actual therapeutic advantage of the combination in comparison with each drug administered alone.

What is claimed is:
1. A synergistic anticancer combined preparation, wherein the cancer is sensitive to the synergistic combination, which comprises a morpholinyl anthracycline of formula (I)

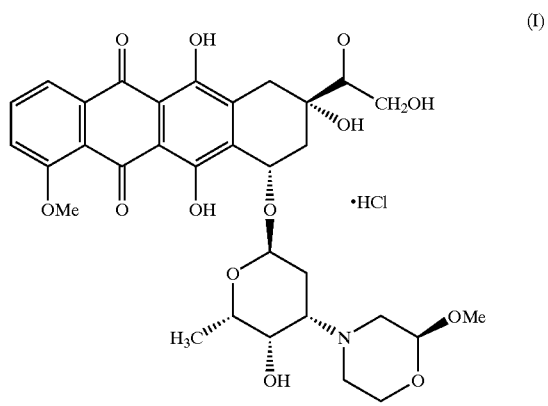

and an anticancer agent selected from the group consisting of an alkylating agent, an antimetabolite, a topoisomerase II inhibitor, a topoisomerase I inhibitor and an antimitotic drug.

2. A preparation according to claim 1, wherein the alkylating agent is selected from the group consisting of mitomycin C, cyclophosphamide, busulfan, ifosfamide, isosfamide, melphalan, hexamethylmelamine, thiotepa, chlorambucil, and dacarbazine.

3. A preparation according to claim 1, wherein the antimetabolite is selected from the group consisting of gemcitabine, capecitabine, 5-fluorouracil, cytarabine, 2-fluorodeoxy cytidine, methotrexate, idatrexate, tomudex and trimetrexate.

4. A preparation according to claim 1, wherein the topoisomerase II inhibitor is selected from the group consisting of doxorubicin, epirubicin, etoposide, teniposide and mitoxantrone.

5. A preparation according to claim 1, wherein the topoisomerase I inhibitor is selected from the group consisting of irinotecan (CPT-11), 7-ethyl-10-hydroxy-camptothecin (SN-38) and topotecan.

6. A preparation according to claim 1, wherein the antimitotic drug is selected from the group consisting of paclitaxel, docetaxel, vinblastine, vincristine and vinorebline.

7. A pharmaceutical composition comprising the preparation according to claim 1, and a pharmaceutically acceptable carrier or excipient.

8. A method of cancer treatment which comprises administering to a mammal a therapeutically effective amount of a morpholinyl anthracycline of formula (I) as defined in claim 1, and an anticancer agent selected from the group consisting of alkylating agent, an antimetabolite, a topoisomerase II inhibitor, a topoisomerase I inhibitor and an antimitotic drug, wherein the morpholinyl anthracycline and the said anticancer agent are administered simultaneously, separately or sequentially to provide a synergistic anticancer effect, and wherein the cancer is sensitive to the synergistic combination.

9. The method according to claim 8, wherein the alkylating agent is selected from the group consisting of mitomycin C, cyclophosphamide, busulfan, ifosfamide, isosfamide, melphalan, hexamethylmelamine, thiotepa, chlorambucil, and dacarbazine.

10. The method according to claim 8, wherein the antimetabolite is selected from the group consisting of gemcitabine, capecitabine, 5-fluorouracil, cytarabine, 2-fluorodeoxy cytidine, methotrexate, idatrexate, tomudex and trimetrexate.

11. The method according to claim 8, wherein the topoisomerase II inhibitor is selected from the group consisting of doxorubicin, epirubicin, etoposide, teniposide and mitoxantrone.

12. The method according to claim 8, wherein the topoisomerase I inhibitor is selected from the group consisting of irinotecan (CPT-11), 7-ethyl-10-hydroxy-camptothecin (SN-38) and topotecan.

13. The method according to claim 8, wherein the antimitotic drug is selected from the group consisting of paclitaxel, docetaxel, vinblastine, vincristine and vinorebline.

14. The method according to claim 8, wherein the anticancer treatment is liver cancer therapy.

15. The method according to claim 14, wherein the liver cancer is a cancer primarily confined to the liver or is a liver metastase.

16. The method according to claim 15, wherein the cancer primarily confined to the liver is a hepatocellular carcinoma or a cholangiocarcinoma.

17. The method according to claim 8, wherein the medicament is formulated for intrahepatic administration.

18. The method according to claim 8, wherein the morpholinyl anthracycline is administered before said anticancer agent.

19. The method according to claim 8, wherein the morpholinyl anthracycline is administered on days 1 and 2 and the said anticancer agent is administered on day 3.

20. A therapeutic kit comprising, in suitable container means, synergistic effective amounts of a synergistic anticancer combination, wherein the cancer is sensitive to the synergistic combination, a pharmaceutical formulation of a morpholinyl anthracycline of formula (I) as defined in claim 1 and an anticancer agent selected from the group consisting of alkylating agent, an antimetabolite, a topoisomerase II inhibitor, a topoisomerase I inhibitor and an antimitotic drug.

21. A kit according to claim 20, wherein the morpholinyl anthracycline and the anticancer agent are present within a single container means.

22. A kit according to claim 20, wherein the morpholinyl anthracycline and the anticancer agent are present within distinct container means.

* * * * *

UNITED STATES PATENT AND TRADEMARK OFFICE
CERTIFICATE OF CORRECTION

PATENT NO. : 6,586,428 B1
DATED : July 1, 2003
INVENTOR(S) : Geroni et al.

It is certified that error appears in the above-identified patent and that said Letters Patent is hereby corrected as shown below:

Column 1,
Lines 6 and 10, delete "theraphy" and replace with -- therapy --.
Line 14, delete "chemotheraphy" and replace with -- chemotherapy --.
Lines 26, 31 and 36, delete "theraphy" and replace with -- therapy --.

Column 2,
Line 18, delete ". HCl" and replace with -- •HCl --.

Column 3,
Lines 2 and 30, delete "theraphy" and replace with -- therapy --.
Line 21, delete "mmls" and replace with -- mammals --.
Line 25, delete "costituents" and replace with -- constituents --.
Lines 49, 54, 58 and 67, delete "costituents" and replace with -- constituents --.

Column 4,
Line 2, delete "costituents" and replace with -- constituents --.
Line 41, delete "theraphy" and replace with -- therapy --.

Column 5,
Line 15, delete "videly" and replace with -- widely --.
Line 35, delete "anthacycline" and replace with -- anthracycline --.
Lines 37, 50 and 59, delete "antimetabolite" and replace with -- antimetabolite, --.

Column 6,
Line 45, delete "m2" and replace with -- $m^2$ --.
Lines 55 and 61, delete "anthacycline" and replace with -- anthracycline --.

UNITED STATES PATENT AND TRADEMARK OFFICE
CERTIFICATE OF CORRECTION

PATENT NO.   : 6,586,428 B1
DATED        : July 1, 2003
INVENTOR(S)  : Geroni et al.

It is certified that error appears in the above-identified patent and that said Letters Patent is hereby corrected as shown below:

Column 7,
Lines 9 and 25, delete "theraphy" and replace with -- therapy --.

Column 8,
Lines 5-20, in claim 1, delete formula (I) and insert the following formula (I):
--
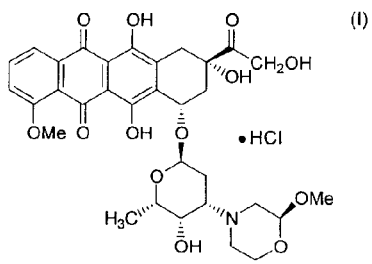
--

Signed and Sealed this

Eleventh Day of November, 2003

JAMES E. ROGAN
*Director of the United States Patent and Trademark Office*